United States Patent [19]

Kaldany

[11] Patent Number: 5,127,419

[45] Date of Patent: Jul. 7, 1992

[54] BIOPSY INSTRUMENT WITH SLOTTED DRIVING MEMBER

[76] Inventor: Antoine Kaldany, 1069 W. Roxbury Pkwy., Chestnut Hill, Mass. 02167

[21] Appl. No.: 724,706

[22] Filed: Jul. 2, 1991

[51] Int. Cl.⁵ .............................................. A61B 10/00
[52] U.S. Cl. ...................................... 128/754; 606/170
[58] Field of Search ............... 128/754, 751, 749, 753, 128/755; 606/167, 170, 184, 185, 187; 604/22, 93, 95, 117, 158, 159, 160, 164, 165, 166, 170

[56] References Cited

U.S. PATENT DOCUMENTS

| | | | |
|---|---|---|---|
| 3,606,878 | 9/1971 | Kellogg, Jr. | 128/753 |
| 4,600,014 | 7/1986 | Beraha | 128/754 |
| 4,609,370 | 9/1986 | Morrison | 604/165 |
| 4,699,154 | 10/1987 | Lindgren | 128/754 |
| 4,702,261 | 10/1987 | Cornell et al. | 128/754 |
| 4,776,346 | 10/1988 | Beraha et al. | 128/754 |
| 4,881,551 | 11/1989 | Taylor | 128/754 |
| 4,907,598 | 3/1990 | Bauer | 128/753 |
| 4,917,100 | 4/1990 | Nottke | 128/749 |
| 4,940,061 | 7/1990 | Terwilliger et al. | 128/754 |
| 4,958,625 | 9/1990 | Bates et al. | 128/754 |
| 4,986,814 | 1/1991 | Burney et al. | 604/164 |

FOREIGN PATENT DOCUMENTS

WO89/10091  11/1989  World Int. Prop. O.
WO91/10399   7/1991  World Int. Prop. O.

Primary Examiner—Max Hindenburg
Assistant Examiner—Guy V. Tucker
Attorney, Agent, or Firm—Hamilton, Brook, Smith & Reynolds

[57] ABSTRACT

A biopsy instrument with a driving member for sequentially advancing a stylet and cannula to cut a core biopsy sample and a process for cutting a tissue sample from within the body of an individual.

12 Claims, 2 Drawing Sheets

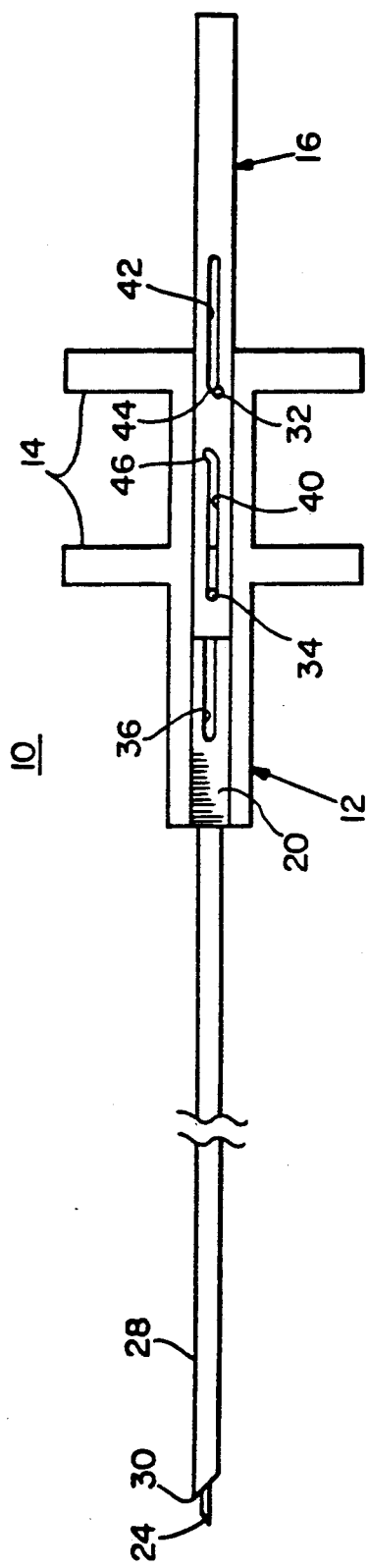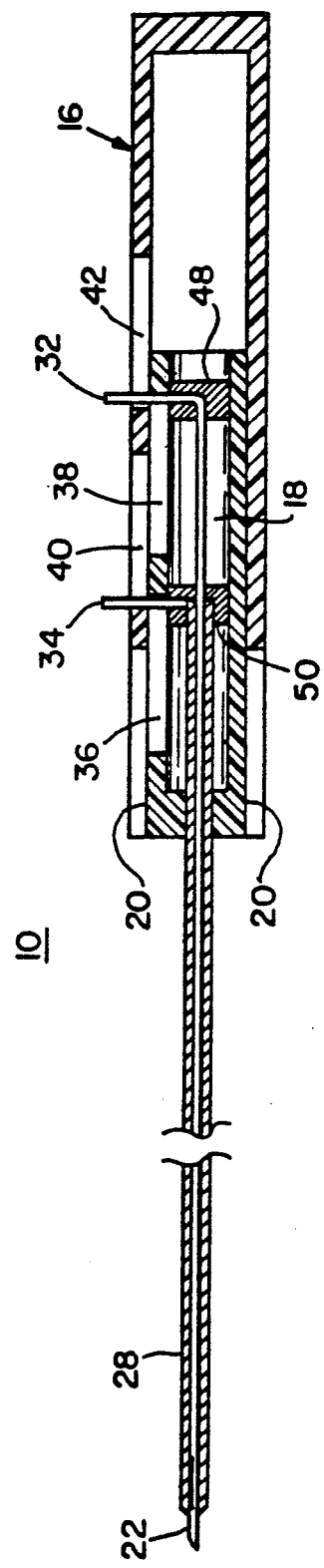

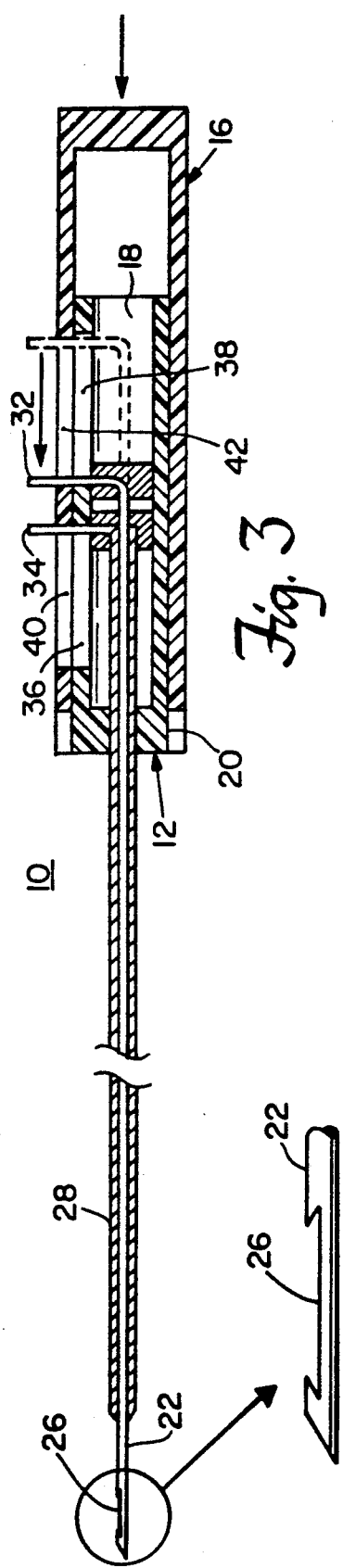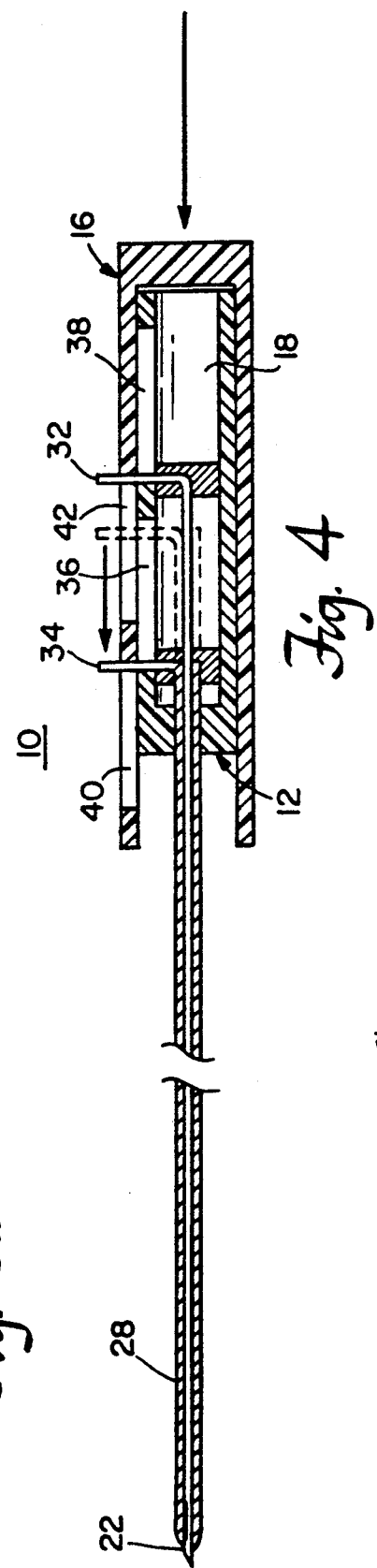

BIOPSY INSTRUMENT WITH SLOTTED DRIVING MEMBER

BACKGROUND OF THE INVENTION

It is often desirable to somehow remove and test a tissue sample, particularly in the diagnosis and treatment of cancerous tumors, pre-malignant conditions and other diseases or disorders. Typically, when the physician establishes by means of procedures such as palpation, x-ray or ultrasound imaging that suspicious circumstances exist, it is important to determine the condition of the cells (e.g. whether the cells are benign or cancerous by performing a tissue biopsy). Biopsy may be done by an open or closed technique. Open biopsy removes the entire mass (excision biopsy) or a part of the mass (incision biopsy). Closed biopsy, on the other hand, is usually done with a needle-like instrument and may be either an aspiration or a core biopsy. In needle aspiration biopsy, individual cells or clusters of cells are obtained for cytologic examination and may be prepared such as in a Papanicolaou smear. In core biopsy, as the term suggests, a core or fragment of tissue is obtained for histologic examination.

The type of biopsy depends in large part on circumstances present with respect to the patient and no single procedure is ideal for all cases. However, core biopsy is extremely useful in a number of conditions and is being used more frequently by the medical profession.

A variety of biopsy instruments and devices have been described and used for obtaining specimens of tissue. For example, reference is made to U.S. Pat. Nos. 4,651,752; 4,702,260; and 4,243,048 which show biopsy instruments of varying types. Additionally, a number of very specialized devices for extracting samples of tissue have been described such as the biopsy device in U.S. Pat. No. 4,461,305, for removing a sample of tissue from the female uterine cervix.

Other devices have been disclosed which relate to surgical cutting instruments. For example, U.S. Pat. No. 4,589,414 discloses an instrument which is particularly designed to operate in the area of the knee to withdraw tissue chips. Also available are so-called biopsy guns for removing a core of tissue. Such guns customarily are spring powered devices and must be cocked with considerable force. When actuated, such guns produce a loud snapping noise, combined with a jerking action. Such a biopsy gun may employ a needle set consisting of an inner stylet and an outer tube called a cannula. The stylet is a needle like device with a notched cut-out at its distal end. The cannula is in effect a hollow needle with an angled cutting surface at its distal end which slides over the stylet. When the stylet is forced into tissue, the tissue is pierced and relaxes into the notched cutout of the stylet. When the cannula is then slid forward, the tissue in the notch of the stylet is sliced off and retained in the notch until the cannula is withdrawn. Examples of such gun devices are shown in U.S. Pat. Nos. 4,600,014 and 4,699,154.

Although such spring powered biopsy guns will remove a core or sample of the tissue, they have rather serious disadvantages. For one, they must be manually cocked with a plunger bar. Such "cocking" of the gun requires considerable force and the gun must be cocked for each biopsy cut. A further disadvantage is that the springs provided in the gun accelerate the needles until a mechanical stop position is reached, creating a loud snapping noise and jerking motion which is a problem both to the physician and the patient. This noise and jerking action can cause the patient to jump and in some cases may prevent the physician from striking the intended tissue target. Another disadvantage is that the force and velocity delivered to the stylet and cannula rapidly diminishes when traveling from a retracted to a fully extended position resulting in tissue samples of lower quality. Furthermore, once the biopsy gun is released, the physician has no control over the instruments function until the biopsy is completed and cannot continue to guide the instrument by feel.

SUMMARY OF THE INVENTION

The subject invention relates to an improved biopsy instrument. The improved biopsy instrument is comprised of a driving member which sequentially advances a stylet and cannula to cut a tissue core biopsy sample. For reference purposes, the end of the device nearest the driving member is referred to as the proximal end and the end of the device having the cutting tip is referred to as the distal end.

The biopsy instrument includes a housing with a bore extending along a longitudinal axis of the housing. A track in the housing extends parallel to the bore. The track has a proximal and distal housing slot extending along the longitudinal axis. A stylet and a cannula are mounted in the bore and extend coaxially along the longitudinal axis. The driving member is slideably engaged in the track for longitudinal movement therein and the driving member also contains a proximal and distal elongate slot. A stylet coupling means extends to the stylet through the proximal elongate slot in the housing and the driving member. A cannula coupling means extends to the cannula through the proximal elongate slot in the housing and the driving member.

With the biopsy instrument in the fully retracted position, the physician places the stylet tip proximate to the tissue to be sampled. As the driving member is moved distally along the track toward the stylet tip, the stylet tip is extended until the stylet coupling means reaches the distal end of the proximal housing slot and as the driving member is moved further along the track the cannula is extended until the cannula coupling means reaches the distal end of the distal housing slot. In this, the fully advanced position, a sample of tissue has been cut by the advancing cannula and the tissue is contained within the resected portion of the stylet.

In an alternative embodiment, referred to as the remote embodiment, the stylet and cannula are extended in length to enable deeper penetration into the body. The stylet and cannula are designed to be flexible and the tip of the stylet tip of the remote embodiment can be modified to prevent injury during insertion.

A significant advantage of the invention is that the physician advances the stylet and cannula sequentially by unidirectional advancement of the driving member in a single, smooth and uninterrupted motion. This facilitates single-handed operation without the need for springs. This offers increased control and "feel", enabling realtime adjustments of the biopsy procedure. This allows the physician to fully utilize his or her expertise thereby decreasing the risk of injury to the patient. In addition, the instrument of the invention produces consistently high quality biopsy samples and is reliable, simple and inexpensive to manufacture. The flexibility afforded by the biopsy instrument enables the production of specialized needles suitable for magnetic resonance imaging (MRI) guided tissue biopsy and CT scan guided biopsy.

BRIEF DESCRIPTION OF THE FIGURES

FIG. 1 is a top view of the biopsy instrument of this invention.

FIG. 2 is a cross-section side view of the biopsy instrument of this invention in the fully retracted position.

FIG. 3 is a cross-section side view of the biopsy instrument of this invention in a partially advanced position.

FIG. 3a is a side view of the distal terminus of the biopsy instrument of this invention.

FIG. 4 is a cross-section side view of the biopsy instrument of this invention in the fully advanced position.

FIG. 5 is a side view of the distal terminus of a preferred embodiment of the remote embodiment of the biopsy instrument in a partially advanced position.

FIG. 6 is a side view of the distal terminus of a preferred embodiment of the remote embodiment of the biopsy instrument in the fully advanced position.

DESCRIPTION OF A PREFERRED EMBODIMENT

Considering now the drawings in detail, FIG. 1 shows a top view of a preferred embodiment of the biopsy instrument. The biopsy instrument 10 has a housing 12 with a pair of fingergrips 14 extending transverse the longitudinal axis of the housing. A driving member 16 is slideably engaged with a track 20 formed along the longitudinal length of housing 12.

Referring to FIG. 2, which is a cross-sectional side view of the preferred embodiment, the housing track 20 has an elongate proximal housing slot 38 and an elongate distal housing slot 36 which extend along the longitudinal axis. The driving member also has an elongate proximal slot 42 and an elongate distal slot 40. The proximal 42 and distal 40 driving member slots are notched at their distal and proximal ends, respectively. The notch in the proximal driving member slot 42 is designated notch 44 and the notch in the distal driving member slot 40 is designated notch 46 (shown most clearly in FIG. 1).

The housing has a cylindrical bore 18 formed therein which extends along the longitudinal axis of the housing 12. Mounted within the cylindrical bore 18 and extending along the longitudinal axis is a stylet 22 and a cannula 28 mounted coaxial to the stylet. The stylet 22 and cannula 28 are secured at their respective proximal ends by a stylet grip 48, and a cannula grip 50. The stylet grip 48 and cannula grip 50 are disc-shaped with a diameter which approximates the diameter of the cylindrical bore. The stylet grip 48 and the cannula grip 50 are slideably engaged within the housing bore 18. The stylet grip 48 and cannula grip 50 have a channel formed therein for engagement of the proximal end of the stylet and cannula respectively.

In the preferred embodiment, the stylet connecting means and the cannula connecting means are drive pins. Stylet 22 and cannula 28 have a respective stylet drive pin 32 and a cannula drive pin 34 attached or formed at a proximal end which extend in a direction perpendicular to the longitudinal axis. Preferably, the cannula drive pin 34 and stylet drive pin 32 are formed from the metal comprising the stylet 22 and cannula 26 by placing a right angle bend in the proximal end of the stylet 22 and cannula 28. The right angle bend in the stylet 22 and cannula 28 is engaged by a right angle channel in the stylet grip 48 and cannula grip 50, respectively.

The stylet drive pin 32 extends in a direction perpendicular to the longitudinal axis and extends through the proximal housing slot 38 and the proximal driving member slot 42. The cannula drive pin 34 extends perpendicularly from the longitudinal axis and extends through the distal housing slot 36 and distal driving member slot 40.

The stylet and cannula are preferably metallic (e.g. stainless steel). Specialized needles, such as needles for use in magnetic resonance guided biopsy, are composed of materials having special properties. Nickel is particularly useful for magnetic resonance applications. The other components of the device, including the housing, driving member, stylet and cannula grips, etc. are preferably manufactured from a plastic material. The use of molded plastic components for the manufacture of the instrument is preferred.

To use the biopsy instrument of this invention to obtain a biopsy sample, the physician begins with the device in the fully retracted position as shown in FIG. 2. In this position, the driving member is withdrawn to its most proximal position. In this position, the cannula drive pin 34 is located at the proximal terminus of housing slot 36 and the distal terminus of driving member slot 40. The stylet drive pin is located at the proximal terminus of housing slot 38 and engaged in the notch 44 at the distal terminus of driving member slot 42.

The distal tip of the device is positioned at a point in the body proximate to the tissue to be sampled. The physician advances the driving member 16 toward the distal end of the device. As the driving member is advanced, the stylet drive pin 32 remains locked in notch 44 resulting in the advance of the distal tip 24 of the stylet 22 into the tissue to be sampled. The cannula drive pin 34, on the other hand, remains stationary. As the driving member 16 advances from the original fully retracted position, the proximal terminus of driving member slot 40 advances toward stationary cannula pin 34.

FIG. 3 shows the relationship of the parts at the point at which the stylet 22 is fully advanced and the cannula 28 is fully retracted. In this position, tissue to be sampled relaxes into the resected portion 26 of the stylet shaft. The cannula drive pin 34 is now in contact with the proximal termini of both driving member slot 40, and housing slot 36. The stylet drive pin 32 is in contact with the distal terminus of housing slot 38, and engages notch 44 at the distal terminus of driving member slot 42.

As the physician continues to advance the driving member distally, the resistance of the housing on stylet drive pin 32 (which has reached the distal terminus of housing slot 38) forces the stylet drive pin out of notch 44 and into driving member slot 42. This results in loss of motion of the stylet 22 and the proximal terminus of driving member slot 42 advances toward the stylet drive pin 32 as the physician continues to advance the driving member 16. At approximately the same time that the stylet drive pin 32 is forced from notch 44, the cannula drive pin 34 begins its distal advance. The cannula drive pin 34 is engaged with notch 46 at the proximal terminus of driving member slot 40. As the driving member 16 is advanced, the cannula drive pin 34 and the cannula 28 itself are driven distally. The cutting edge 30 of the cannula cuts tissue as the cannula advances.

FIG. 4 shows the instrument 10 with the driving member 16 in the fully advanced position. At this point the cannula drive pin 34 and the stylet drive pin 32 are both at the proximal termini of driving member slots 40 and 42, respectively. The cannula 28 is fully advanced and the cutting edge 30 has traveled along the stylet 22 to a point at which the resected portion 26 of the stylet shaft is no longer exposed and any tissue which had previously relaxed into the resected portion 26 of the stylet shaft has been completely severed and is contained within the intersticial space between the stylet and cannula.

The physician can now withdraw the biopsy instrument from the body. When the biopsy instrument is withdrawn, the driving member is retracted proximally to expose the biopsy tissue in the resected portion of the stylet. The biopsy tissue is then subjected to appropriate analysis.

An alternative embodiment, referred to as the remote embodiment, is designed for deeper penetration into the body. The shaft of the stylet and cannula are elongate and are made from a semi-rigid material so that bends can be introduced during insertion, for example, to avoid possible contact with vital organs. The mechanism of sequential stylet and cannula advance is identical in the remote embodiment to that described above.

FIGS. 5 and 6 show an alternative stylet tip for use in the remote embodiment. The stylet tip 24 is rounded to prevent cutting injury. The points of contact between the distal terminus of the cannula and the stylet tip have serrated edges 54 which engage and cut a biopsy sample from the tissue of interest. One skilled in the art will recognize that a variety of stylet tip designs are useful for use in connection with the subject invention. The tip designs shown in the drawings are meant to be examples only.

EQUIVALENTS

Those skilled in the art will know, or be able to ascertain using no more than routine experimentation, many equivalents to the specific embodiments of the invention described herein. These and all other equivalents are intended to be encompassed by the following claims.

I claim:

1. A biopsy instrument comprising:
   a) a housing with a bore extending along a longitudinal axis of the housing and a track extending parallel to the bore, said track having an elongate proximal housing slot and an elongate distal housing slot extending along the longitudinal axis;
   b) a stylet having a distal tip end and a cannula mounted coaxially thereto and within the bore and extending along the longitudinal axis thereof;
   c) a driving member slideably engaged in said track for longitudinal movement therein, the driving member having a proximal elongate slot with a notch formed therein and a distal elongate slot with a notch formed therein, said slots extending along the longitudinal axis;
   d) a stylet drive pin for engaging the stylet with the driving member, the stylet drive pin extending from the stylet in a direction perpendicular to the longitudinal axis through the proximal housing slot and the proximal driving member slot;
   e) a cannula drive pin for engaging the cannula with the driving member, the cannula drive pin extending from the cannula in a direction perpendicular to the longitudinal axis through the distal housing slot and the distal driving member slot whereby as the driving member is moved distally along the track toward the stylet tip end, the stylet is engaged by the stylet drive pin and extended until the stylet drive pin reaches the distal end of the proximal housing slot and as the driving member is moved further along the track the cannula is engaged by the stylet drive pin and extended until the cannula drive pin reaches the distal end of the distal housing slot.

2. A biopsy instrument of claim 1 wherein the proximal terminus of the stylet is mounted within a stylet grip and the proximal terminus of the cannula is mounted within a cannula grip, the stylet grip and the cannula grip being engaged slideably within the housing bore.

3. The instrument of claim 1 wherein the notch in the proximal slot is located at a distal end of the proximal slot for engaging the stylet drive pin and the notch in the distal slot is located at a proximal end of the distal slot for engaging the cannula drive pin.

4. The instrument of claim 3 wherein the stylet has a tip with a resected portion adjacent the tip.

5. The instrument of claim 4 wherein the housing has finger grips extending therefrom transverse said longitudinal axis.

6. A biopsy instrument comprising:
   a) a housing with a bore extending along a longitudinal axis of the housing and a track extending parallel to the bore, said track having an elongate proximal housing slot and an elongate distal housing slot extending along the longitudinal axis;
   b) a driving member slideably engaged in said track for longitudinal movement therein, the driving member having a proximal elongate slot with a notch located at a distal end of the proximal slot for engaging a stylet drive pin and a distal elongate slot with a notch located at a proximal end of the distal slot for engaging a cannula drive pin extending along the longitudinal axis; and
   c) a stylet and a cannula mounted within the bore and extending along the longitudinal axis thereof, the proximal end of the stylet and cannula being bent in a direction perpendicular to the longitudinal axis to form said respective stylet and cannula drive pins, the stylet drive pin extending through the proximal housing slot and the proximal driving member slot, the cannula drive pin extending through the distal housing slot and the distal driving member slot.

7. A biopsy instrument of claim 6 further comprising a stylet grip and a cannula grip engaged slideably within the bore, the stylet grip and the cannula grip having a channel formed therein for engagement with the proximal end of the stylet and cannula, respectively.

8. A biopsy instrument comprising:
   a) a housing with a bore extending along a longitudinal axis of the housing and a track extending parallel to the bore, said track having an elongate proximal slot and an elongate distal slot extending along the longitudinal axis;
   b) a driving member slideably engaged in said track for longitudinal movement therein, the driving member having a proximal elongate slot with stylet engagement means therein for engaging a stylet drive pin and a distal elongate slot with cannula engagement means therein for engaging a cannula drive pin, said slots extending along the longitudinal axis;

c) a stylet and a cannula supported at a proximal end by a respective stylet grip and a cannula grip, the stylet and cannula grip slideably engaged within the bore;

d) a stylet drive pin for engaging the stylet with the driving member, the stylet drive pin extending in a direction perpendicular to the longitudinal axis from the stylet grip through the proximal housing slot and the proximal driving member slot for engagement with the stylet engagement means; and a cannula drive pin for engaging the cannula with to the driving member, the cannula drive pin extending in a direction perpendicular to the longitudinal axis from the cannula grip through the distal housing slot and the distal driving member slot for engagement with the cannula engagement means.

9. A remote biopsy instrument comprising:

a) a housing with a bore extending along a longitudinal axis of the housing and a track extending parallel to the bore, said track having an elongate proximal slot and an elongate distal slot extending along the longitudinal axis;

b) an elongate flexible stylet and an elongate flexible cannula mounted coaxially thereto and within the bore and extending along the longitudinal axis thereof;

c) a driving member slideably engaged in said track for longitudinal movement therein, the driving member having a proximal elongate slot and a distal elongate slot extending along the longitudinal axis with stylet engagement means, notched in said proximal slot and cannula engagement means notched in said distal slot;

d) a stylet member on the stylet, the stylet member extending from the proximal end to the stylet in a direction perpendicular to the longitudinal axis through the proximal housing slot and the proximal driving member slot for engagement with the stylet engagement means; and e) a cannula member on the cannula, the cannula member extending from the proximal end of the cannula in a direction perpendicular to the longitudinal axis through the distal housing slot and the distal driving member slot for engagement with the cannula engagement means.

10. A remote biopsy instrument of claim 9 wherein the distal tip of the stylet is blunt to prevent injury during insertion.

11. A process for cutting and obtaining a tissue sample from within the body of an individual comprising:

a) assembling a cannula coaxially about a stylet within a longitudinally extending bore of a housing for longitudinal movement along said bore;

b) engaging the stylet with a driving member having an elongate proximal slot and an elongate distal slot, the driving member being mounted on a track in the housing for longitudinal movement, the track having an elongate proximal slot and an elongate distal slot, the stylet being engaged with the driving member via a coupling means which is connected to the proximal end of the stylet and extends through the proximal housing slot and the proximal driving member slot and thereby connects the proximal end of the stylet to the driving member;

c) engaging the cannula with the driving member, the cannula being engaged with the driving member via a coupling means which is connected to the proximal end of the cannula and extends through the distal housing slot and the distal driving member slot and thereby connects the cannula to the driving member;

d) advancing the driving member partially until the stylet coupling means reaches the distal end of the proximal housing slot at which point the stylet is fully advanced exposing a resected portion of the stylet shaft;

e) advancing the driving member fully until the cannula coupling means reaches the distal end of the distal housing slot at which point the cannula is fully advanced and any tissue which had relaxed into the resected portion of the stylet shaft has been severed; and f) retracting the driving member to resect the severed portion.

12. A process for cutting a tissue sample from within the body of and individual comprising:

a) assembling a cannula coaxially about a stylet within a longitudinally extending bore of a housing for longitudinal movement along said bore;

b) engaging the stylet with a driving member having an elongate proximal slot and an elongate distal slot, the driving member being mounted on a track in the housing for longitudinal movement, the track having an elongate proximal slot and an elongate distal slot, the proximal end of the stylet containing a bend which results in the extension of the proximal end of the stylet in a direction perpendicular to the longitudinal axis, the proximal end extending through the proximal housing slot and the proximal driving member slot thereby connecting the stylet to the driving member;

c) engaging the cannula with the driving member, the proximal end of the cannula containing a bend which results in the extension of the proximal end of the cannula in a direction perpendicular to the longitudinal axis, the proximal end extending through the distal housing slot and the distal driving member slot thereby connecting the cannula to the driving member;

d) advancing the driving member and thereby the stylet tip until the proximal end of the stylet reaches the distal end of the proximal housing slot at which point the stylet is fully advanced exposing a resected portion of the stylet shaft; and e) advancing the driving member further until the proximal end of the cannula reaches the distal end of the distal housing slot at which point the cannula is fully advanced and any tissue which had relaxed into the resected portion of the stylet shaft has been severed.

* * * * *